(12) United States Patent
Stier

(10) Patent No.: US 6,569,439 B1
(45) Date of Patent: May 27, 2003

(54) PROCESS FOR MAKING PERSONAL CARE COMPOSITIONS COMPRISING TITANIUM DIOXIDE AND PERSONAL CARE COMPOSITIONS MADE BY THE PROCESS

(75) Inventor: Roger E. Stier, Clifton, NJ (US)

(73) Assignee: Noville Inc., South Hackensack, NJ (US)

( * ) Notice: Subject to any disclaimer, the term of this patent is extended or adjusted under 35 U.S.C. 154(b) by 0 days.

(21) Appl. No.: 10/010,362

(22) Filed: Nov. 13, 2001

(51) Int. Cl.[7] .......................... A61K 7/00; A61K 33/24; A01N 59/16
(52) U.S. Cl. .................................. 424/401; 424/617
(58) Field of Search .................................. 424/401, 617

(56) References Cited

U.S. PATENT DOCUMENTS 5,328,682 A * 7/1994 Pullen et al. .................. 424/49
5,531,983 A * 7/1996 Van Velthuijsen ........... 424/49

* cited by examiner

*Primary Examiner*—Alton N. Pryor
(74) *Attorney, Agent, or Firm*—Norris McLaughlin & Marcus

(57) ABSTRACT

The invention concerns a process for making personal care compositions and opacifying agents, and corresponding products, having a stable cloudy and milky appearance. The components are processed in a specific sequence in which titanium dioxide is added after thickening agent which comprises a hydrophilic colloid. The composition may, optionally, comprise calcium lactate, calcium lactate salts and combinations thereof. The products, and process, may also comprise the addition of other components such as filler, additives, colorants, cooling agents, warming agents, numbing agents, additional flavorings, active compounds, pharmaceutical actives and excipients or finished bases.

40 Claims, No Drawings

PROCESS FOR MAKING PERSONAL CARE COMPOSITIONS COMPRISING TITANIUM DIOXIDE AND PERSONAL CARE COMPOSITIONS MADE BY THE PROCESS

BACKGROUND OF THE INVENTION

1. Field of the Invention

The invention concerns a process for making personal care compositions and personal care compositions made by the process, such as oral hygiene compositions, pharmaceutical compositions and the like. The invention also concerns a process for making an opacifying agent that can be used with finished bases to make cloudy and milky consumer care products and/or comestible goods. The components are processed in a specific sequence of steps to obtain a composition having a cloudy and milky, e.g. opaque, appearance as a result of the suspension of titanium dioxide in the composition. The cloudy and milky appearance is attained by first combining water, humectant and, optionally, other ingredients then adding one or more thickening agents and then adding titanium dioxide. The finished products, which also include other components such as fillers, additives, colorants, cooling agents, warming agents, numbing agents, additional flavorings, active compounds and the like, maintain a stable cloudy and milky appearance in long term use and storage.

2. The Prior Art

One drawback encountered in the art with personal care compositions having a cloudy and milky appearance is the ability to form a stable suspension or emulsion such that the clouding and/or whitening agent remains in suspension in the product without the consumer agitating the product, such as by shaking the container. Products that maintain a cloudy and milky appearance during storage in a retail environment and during the useful product life are preferred over products requiring agitation to achieve a cloudy and milky appearance. From a marketability viewpoint, products that cannot maintain a cloudy and milky appearance may have impaired consumer acceptance compared to those products that remain cloudy and milky during storage on a retail shelf.

U.S. Pat. No. 5,328,682 describes abrasive oral hygiene compositions that do not experience sedimentation of the solid abrasive particles over long term storage. These compositions have suspending agents comprising synthetic and natural clays.

There is growing consumer demand for products containing calcium, as calcium is an essential element in the diet of all segments of society, particularly women and children. Calcium lactate and salts of calcium lactate are a source for dietary calcium and the ability to include calcium lactate in a personal care composition having a stable cloudy and milky appearance is attractive from a marketability viewpoint because of the natural association between milk and calcium.

In an embodiment of the invention, the personal care composition is in the form of oral hygiene compositions, such as mouthwashes and rinses, toothpaste, gels, powders, gums, mouth sprays and lozenges, which are directed, completely or in part, towards alleviating the conditions in the mouth which cause malodor, generally by physical means, such as brushing teeth with a dentifrice, or chemical means involving the application of mouthwashes or mouth rinses. Oral malodor, plaque, gingivitis, periodontal disease, and discoloration of the teeth, are all undesirable conditions that affect many people. Malodor of the oral cavity is also known as halitosis or bad breath and it is generally believed that the cause of this condition is due to the presence of anaerobic bacteria, especially gram-negative anaerobic bacteria, in the mouth. These bacteria will generate volatile sulfur compounds (VSC) which are known to cause breath malodor.

Oral malodor not only comes from the posterior dorsal surface of the tongue but also from periodontal pockets. A person with gingivitis or periodontal disease may have increased oral malodor from disintegrated epithelial cells. Epithelial cells turn over faster if inflammation is present. Therefore, a larger number of these dead epithelial cells remain in the oral cavity and will degrade into the malodorous compounds. In addition VSC will also alter the epithelial barrier, permitting penetration of the barrier by antigenic substances.

Oral hygiene compositions have traditionally been in the form of clear solutions, examples of which are commercially available products like those from Proctor & Gamble, Cincinnati, Ohio, U.S.A., under the trademark SCOPE® and from the Warner Lambert Consumer Group of Pfizer, Morris Plains, N.J., U.S.A. under the trademarks LISTERINE® and PLAX®. Increasingly, however, there has been consumer demand for new and interesting oral hygiene compositions, such as those having a cloudy and milky appearance.

In U.S. Pat. No. 5,531,983, it was recently disclosed that calcium lactate and calcium lactate salts are effective in combating tartar formation on teeth. The inclusion of calcium lactate in oral hygiene compositions having a cloudy and milky appearance is particularly attractive because such compositions would serve to provide both oral care and a source of calcium in the diet, and have the beneficial consumer association between calcium and milk.

In another preferred embodiment of the invention, the personal care composition is used for treating upper gastrointestinal tract distress, such as heartburn, indigestion, stomach ache and the like. Inclusion of calcium in such compositions has the added benefit of providing enhanced acid relief to the user.

In yet another ebodiment of the invention, the process can be modified to result in an opacifying agent which can be used, optionally in concentrated form, with finished bases to form an end product. This opacifying agent may be used in a wide variety of consumer care products and comestible goods, and may also provide whitening properties.

It was an object of the invention to develop personal care compositions, such as oral care compositions and pharmaceutical compositions for treating upper gastrointestinal tract distress, having a cloudy and milky, e.g opaque, appearance.

It was a further object of the invention to develop a process for making personal care compositions having a stable cloudy and milky appearance such that the clouding and/or whitening agents would not settle during the expected useful life of the product.

It was yet another object of the invention to develop a process for making personal care compositions having a stable cloudy and milky appearance that include calcium lactate.

It was still a further object of the invention to provide for making an opacifying agent that can be used, either full strength or as a concentrate, as a component of consumer care products or comestible goods to opacify and/or whiten, and an object of the invention was to develop such opacifying agents.

These and other objects of the invention are achieved by a process wherein personal care compositions are made by making a water phase by first dissolving sweetener in water and humectant, then adding thickening agent and then adding titanium dioxide, and then combining the water phase with an oil phase. Calcium lactate can be included in the composition by incorporation in the water phase after the addition of the titanium dioxide. Additives and fillers may also be included in the composition. The personal care composition will retain a cloudy and milky appearance without any, or significant, agitation during long term use and storage, such as during the expected useful life of the composition.

Also, objects of the invention were achieved by modifying the process for making the water phase to obtain the opacifying agent. The opacifying agent can be included in a wide variety of consumer care products and comestible goods as an opacifying agent and/or whitening agent and provides the product with a stable cloudy and milky appearance without any, or significant, agitation during long term use and storage.

In the present Specification, all parts and percentages are on a weight by weight basis unless otherwise noted.

SUMMARY OF THE INVENTION

The personal care compositions are made by combining a water phase and an oil phase. The water phase is made by first mixing water and humectant and at least one sweetener, then adding at least one thickening agent and then adding titanium dioxide in order to obtain a cloudy and milky liquid wherein the titanium dioxide is suspended in the liquid, particularly in a gel matrix formed by components of the thickening agent, and will not settle out. If the personal care composition includes calcium lactate, the calcium lactate is included in the water phase but must be added after the addition of the titanium dioxide. The oil phase is made by combining at least one humectant, such as glycerin and, optionally, one or more flavorings, such as flavoring oils, together with ethoxylated hydrogenated castor oil. The water phase is then combined with the oil phase, and the phases are mixed together to obtain the personal care composition.

The personal care compositions may also comprise fillers, additives, colorants, cooling agents, warming agents, numbing agents, additional flavorings, active compounds and the like, as well as pharmaceutical actives and excipients. These may be incorporated into either the water phase after the addition of the titanium dioxide, or the oil phase or in the composition after the water and oil phases are combined.

The thickening agent preferably comprises at least one hydrophilic colloid, most preferably xanthan gum, which forms a gel upon mixing with the water, thereby forming a gel matrix within the composition. Adding the titanium dioxide after the addition of the thickening agent provides a gel matrix within the composition that traps the titanium dioxide prohibiting or reducing settling of the titanium dioxide and thereby allowing the titanium dioxide to remain in suspension and maintain the cloudy and milky appearance in the personal care composition.

The process may be modified to obtain an opacifying agent which then may be used in a wide variety of consumer care products or comestible goods to provide a stable cloudy and/or milky appearance. The opacifying agent is obtained by making the water phase without the addition of a sweetener. The opacifying agent comprises the gel matrix which traps the titanium dioxide. The opacifying agent can be used, either full strength or in concentrated form, with finished bases for consumer care products or comestible goods.

DETAILED DESCRIPTION OF THE INVENTION

The invention concerns a process for making personal care compositions having a stable cloudy and milky appearance, e.g. an opaque appearance. The cloudy and milky appearance results from the suspension of titanium dioxide in the compositions. During the expected life of the personal care compositions, the titanium dioxide remains in suspension and there is none, or little, settling of titanium dioxide. The personal care compositions may be in the form of personal care products, such as oral hygiene compositions, pharmaceutical compositions and the like and may also be in the form of soaps, shampoos, body washes, lotions, cosmetics, perfumes, foods and the like. Preferred oral hygiene compositions include mouthwashes and rinses, toothpaste, gels, powders, gums, mouth sprays and lozenges. Pharmaceutical compositions are those having a liquid vehicle for the delivery of a pharmaceutical active, particularly in the form a suspension or emulsion, such as antacids, cold and cough medicines, allergy medicines, pain relievers, medicines and the like. In addition, the invention concerns a process for making opacifying agents, and agents made by the process, which can be used, optionally in concentrated form, with finished bases to provide stable opacifying and/or whitening properties to consumer care products and comestible goods, such as soaps, shampoos, hair care products, body washes, lotions, cosmetics, perfumes, beverages, sauces, gravies, comestible food and the like.

The oral care composition is made by separately creating a water phase and an oil phase, and combining the phases. The process for making the oral care composition comprises the steps of:

1. Creating a water phase in a first means for mixing, such as a mixer or blender, by first combining about 30% to about 80% water and about 0.01% to about 0.50% of at least one sweetener, preferably saccharin, together with about 2% to about 25% of at least one water phase humectant, and mixing, preferably for about 5 minutes to about 20 minutes at ambient temperature, then adding about 0.01% to about 0.50% of at least one thickening agent dispersed in about 2.5% to about 10% of a carrier, such as glycerin, polyethylene glycol or combinations thereof, and the like, and continue mixing, preferably for about 5 minutes to about 20 minutes at ambient temperature, then adding about 0.01% to about 1.0% titanium dioxide (TiO$_2$) and continue mixing, preferably for about 5 minutes to about 20 minutes at ambient temperature. Calcium lactate, calcium lactate salts or combinations thereof, in an amount of about 0.5% to about 10% can be added to the water phase after the addition of the titanium dioxide with continued mixing, preferably for about 10 minutes to about 30 minutes at ambient temperature.

2. Separately creating an oil phase by mixing in a second means for mixing, such as a mixer or blender, about 0.1% to about 3.0% of at least one surfactant, preferably ethoxylated hydrogenated castor oil, about 0.01% to about 1.0% of at least one flavoring agent, such as a flavoring oil and, about 1.0% to about 10.0% of at least one oil phase humectant and mixing, preferably for about 5 minutes to about 20 minutes at ambient temperature. In a modification of the process, from about 1.0% to about 30% of alcohol, such as ethyl alcohol, can be incorporated into the oil phase in addition to the humectant and/or surfactant.

3. Combining the water phase and oil phase in either the first or second means for mixing, or a separate means for mixing, preferably for a period of about 5 minutes to about 20 minutes at ambient temperature.

The personal care compositions made by the process described herein will generally comprise about 30% to about 80% water, about 0.01% to about 0.50% of at least one sweetener, about 0.01% to about 0.50% of at least one thickening agent having at least one hydrophilic colloid dispersed in about 2.5% to about 10% carrier, such as glycerin, polyethylene glycol or combinations thereof and the like, about 0.01% to about 1% titanium dioxide, about 2% to about 25% of at least one water phase humectant, about 0.1% to about 3% of at least one surfactant, about 0.01% to about 1% of at least one flavoring agent and about 1.0% to about 10.0% of at least one oil phase humectant. The compositions may also comprise the optional ingredient of about 1.0% to about 10% calcium lactate, calcium lactate salts or combinations thereof.

The process for making the water phase can be modified to obtain an opacifying agent that can be used at either regular strength or in concentrated form with finished bases for consumer care products and comestible goods to provide such products and goods with a stable cloudy and/or milky appearance. The process comprises the same components and processing sequence as used to make the water phase for the personal care composition, except that no sweetener is used. Specifically, the process for making the opacifying agent comprises combining, in a means for mixing, about 30% to about 80% water and about 2% to about 25% of at least one water phase humectant and mixing, preferably for about 5 minutes to about 20 minutes at ambient temperature, then adding about 0.01% to about 0.50% of at least one thickening agent having at least one hydrophilic colloid dispersed in about 2.5% to about 10% of a carrier such as glycerin, polyethylene glycol or combinations thereof, and the like, and continue mixing, preferably for about 5 minutes to about 20 minutes at ambient temperature then adding about 0.01% to about 1.0% titanium dioxide and continue mixing, preferably for about 5 minutes to about 20 minutes at ambient temperature, to obtain the opacifying agent. The opacifying agent made by this process will generally comprise about 30% to about 80% water, about 2% to about 25% of at least one water phase humectant, about 0.01% to about 0.50% of at least one thickening agent dispersed in about 2.5% to about 10% of a carrier, such as glycerin, polyethylene glycol, combinations thereof, and the like, and about 0.01% to about 1.0% titanium dioxide. Also, the process for making the opacifying agent may include adding about 0.5% to about 10% calcium lactate, calcium lactate salts or combinations thereof with continued mixing after the addition of the titanium dioxide with continuous mixing, in which event the opacifying agent will also comprise about 0.5% to about 10% calcium lactate, calcium lactate salts or combinations thereof.

The processing sequence is necessary to obtain the personal care compositions having a stable cloudy and milky appearance, and the opacifying agents which provide the stable cloudy and milky appearance in end products when combined with finished bases. The cloudy and milky appearance is attributable to the gel forming properties of the thickening agent. The thickening agent comprises at least one hydrophilic colloid which forms a gel when added to the water phase which provides a matrix to entrap the insoluble titanium dioxide in the water phase. The gel and titanium dioxide form a complex that allows the titanium dioxide to remain in suspension in the product over the long term notwithstanding the addition of other components to the composition or external forces, such as movement and gravity which can cause settling of suspended particles. This property provides the personal care composition and opacifying agent with the ability to maintain a cloudy and/or milky, opaque, appearance during the expected life of a personal care composition, or the product formed from the finished base, as the gel matrix prohibits or reduces settling of titanium dioxide in the composition.

We have found that use of other clouding agents in the process do not result in a composition that maintains a cloudy, and in particular, a milky, e.g. opaque, appearance over the long term. It appears that the thickening agent comprising a hydrophilic colloid forms the gel matrix that interacts with the titanium dioxide in a manner different from the interaction, if any, of the matrix with other clouding agents.

The processing sequence set forth above is essential to create and/or maintain the cloudy and milky suspension when calcium lactate and/or calcium lactate salts are included in the composition. If the processing sequence with respect to the water phase is not followed, the cloudy and milky appearance is either not achieved or not maintained. The inventors theorize, although they do not wish to be bound to any theory, that this may be the result of either 1) a scattering effect that occurs because of the dipole moment of the titanium dioxide resulting from a shift in electron density that causes the titanium dioxide to scatter in the presence of calcium lactate and/or calcium lactate salts or 2) that the calcium lactate and/or calcium lactate salts affect gel formation of the thickening agent and thus inhibiting or prohibiting the formation of the matrix to entrap the titanium dioxide.

The personal care compositions may also comprise fillers, additives, colorants, cooling agents, warming agents, numbing agents, additional flavorings, active compounds and the like, as well as pharmaceutical actives and excipients. These may be incorporated into the water phase after the addition of the titanium dioxide with continued mixing for a period of about 5 minutes to about 20 minutes at ambient temperature. Alternatively the fillers, additives, colorants, cooling agents, warming agents, numbing agents, additional flavorings, active compounds, pharmaceutical actives, excipients and the like can be mixed with the components of the oil phase before combination of the water and oil phases, or these components can be added to the combined water and oil phases and mixed to obtain the personal care composition.

Titanium dioxide is a white inorganic powder that is found in nature, and can be prepared by methods such as the direct combination of titanium and oxygen, treatment of titanium salts or by chemical reaction or hydrolysis. Titanium dioxide is generally available from Whittaker, Clark & Daniels, South Plainfield, N.J., U.S.A. The titanium dioxide becomes suspended in the personal care composition, particularly within the gel matrix formed by the thickening agent, and provides the cloudy and milky appearance. We have found that conventional clouding agents such as calcium citrate, esters of wood rosin, vegetable gum emulsion, caprylic/capric triglycerides like those available from Stepan Company, Northfield, Ill., USA under the trade name NEOBEE® and high-stability oils will not maintain a stable cloudy and/or milky appearance.

Any food grade and/or pharmaceutically acceptable sweetener maybe used in the water phase, including saccharin, fructose, xylitol, saccharin salts, thaumatin, aspartame, D-tryptophan, dihydrochalcones, acesulfame and cyclamate salts, especially sodium cyclamate and sodium saccharin, and combinations thereof. The most preferred sweetener is saccharin.

Any food grade or pharamcetucially acceptable thickening agent may be used, preferably those which comprise a hydrophilic colloid which forms a gel when added to the water phase and the thickening agent is preferably dispersed in a carrier. The preferred thickening agent is xanthan gum dispersed in glycerin. Other acceptable thickening agents are polymeric polyester compounds, natural gums (e.g. gum karaya, gum arabic, gum tragacanth), carrageenan, hydroxymethyl cellulose, methyl cellulose, carboxymethylcellulose, arrowroot powder, starches, particularly corn starch and potato starch and the like, either alone or with a carrier such as glycerin, polyethylene glycol or combinations thereof, and the like. The thickening agent may comprise combinations of these hydrophilic colloids. Generally, the thickening agent will comprise up to about 5% hydrophilic colloid and about 95.0% to about 99.9% carrier, preferably from about 0.1% to 1.0% hydrophilic colloid and about 99.0% to about 99.9% carrier, based on the total weight of the thickening agent/carrier dispersion.

Calcium lactate and calcium lactate salts are white crystalline powders, and any calcium lactate or salt that is acceptable for food or pharmaceutical applications may be used. Calcium lactate and calcium lactate salt are effective against tartar buildup and, thus, can serve to provide an active ingredient in embodiments where the personal care composition is in the form of oral hygiene compositions, and also provides a source of calcium for the personal care composition. Calcium lactate is available from Purac—North America, Lincolnshire, Ill., U.S.A. under the trade name PURACAL®.

Humectants are used in both the water phase and oil phase. As would be understood by one skilled in the art, a humectant is a substance that absorbs and promotes the retention of moisture from the air. The water phase humectents include glycerin and edible polyhydric alcohols and polyols such as glycerol, diglycerol, propylene glycol, propylene glycol glycerol, isomalt, xylitol, maltitol, sorbitol, mannitol and the like, and combinations thereof. The oil phase humectants include glycerin and edible polyhydric alcohols and polyols such as glycerol, diglycerol, propylene glycol, propylene glycol glycerol, isomalt, xylitol, maltitol, sorbitol, mannitol and the like, and combinations thereof. Polyhdric alcohols and polyols are generally available from SPI Polyols, Inc., New Castle, Del., U.S.A., and glycerin is available from many sources including Rierden Chemicals Trading Company, Libertyville, Ill., U.S.A.

The oil phase comprises a surfactant, including those selected from the group consisting of ethoxylated hydrogenated castor oil, polyoxyethylene sorbitol monolaruin, polyoxyethylene sorbitol monopalmitate, polyoxyethylene sorbitol monostearin, polyoxyethylene sorbitol monolein, polysorbate 20–80, block polymers of polyoxyethylene and polyoxypropylene having a molecular weight between about 1,000 and about 15,000, combinations thereof and the like. Ethoxylated hydrogenated castor oils are available from BASF, Mount Olive, N.J., U.S.A. under the tradename CREMOPHOR® RH and examples of block copolymers available for the invention are poloxamer 407 and PLURONIC® F-127 from BASF. In addition, any other food grade or pharmaceutically acceptable surfactant, emulsifying agent or solubilizing agent may be used.

Flavoring agents useful for the invention are any food grade or pharmaceutically acceptable flavoring agent. Preferably, the flavoring agent comprises natural flavoring oils, including those selected from the group consisting of oil of peppermint, oil of wintergreen, oil of spearmint, clove bud oil, parsley oil, eucalyptus oil and the like. Combinations of oils can also be used. The flavoring agents may comprise compounds selected from the group consisting of menthol, menthane, anethole, methyl salicylate, eucalyptol, cassia, 1-methyl acetate, sage, eugenol, oxanone, alphairisone, marjoram, lemon, orange, propenyl guaethol acetyl, cinnamon, vanilla, thymol, linalool, cinnamaldehyde glycerol acetal and the like, and combinations thereof. The flavoring agent may comprise combinations of natural flavoring oils and other flavoring agents such as the compounds identified above. The flavoring agents are preferably added to the oil phase, however, flavoring agents can be added with the additives, fillers and other ingredients whether or not flavoring agents are incorporated into the humectant phase.

The fillers and additives may include bulking agents, binders, carriers and the like. The additives may include coloring agents or dyes, or colorants, that are acceptable for use in foods, pharmaceuticals or other comestible goods, as would be understood to one skilled in the art. These colorants include Food, Drug and Cosmetic (FD&C) colorants including primary FD&C Blue No. 1, FD&C Blue No. 2, FD&C Green No. 3, FD&C Yellow No. 5, FD&C Yellow No. 6, FD&C Red No. 3, FD&C Red No. 33 and FD&C Red No. 40 and lakes FD&C Blue No. 1, FD&C Blue No. 2, FD&C Yellow No. 5, FD&C Yellow No. 6, FD&C Red No. 2, FD&C Red No. 3, FD&C Red No. 33, FD&C Red No. 40 and combinations thereof.

Examples of cooling agents useful for the invention are those comprising menthol, N-substituted p-menthane-3-carboxamides (such as N-ethyl p-methane-3-carboxamide), 3,1-methoxy propane 1,2-diol and the like. Warming agents include capsicum and nicotinate esters, such as benzyl nicotinate. Numbing agents include benzocaine, lidocaine, clove bud oil, and ethanol.

In a preferred embodiment of the invention, the personal care composition is in the form of an oral hygiene product such as mouthwashes and rinses, toothpaste, gels, powders, gums, mouth sprays, lozenges and the like. These oral hygiene compositions may also comprise active compounds as additives, such as those compounds which mask oral malodor, attack the chemicals that bring about the oral malodor or kill and/or inhibit growth of the bacteria in the mouth which causes breath malodor or halitosis, or pharmaceutical active ingredients. Active compounds include chlorine dioxide, fluoride, alcohols, triclosan, domiphen bromide, cetyl pridinium chlorine and the like, and combinations thereof, in addition to the calcium lactate and calcium lactate salts discussed above.

In another preferred embodiment, the personal care composition is in the form of pharmaceutical compositions or medicine, such as a liquid suspension or emulsion antacid comprising pharmaceutically active agents for treating upper gastrointestinal tract distress which are safe and effective when administered orally for treating disorders of the upper gastrointestinal tract (typically the stomach and/or esophagus) which result in symptoms of upper gastrointestinal tract distress. Such active pharmaceutical agents include antacid agents and acid secretion prevention agents (e.g., $H_2$ receptor-blocking antisecretory agents). Antacid agents include, for example, aluminum carbonate, aluminum hydroxide, aluminum phosphate, aluminum hydroxycarbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumina silicates, magnesium carbonate, magnesium glycinate, magnesium hydroxide, magnesium oxide, magnesium trisilicate, sucralfate, and mixtures thereof. Examples of acid secretion prevention agents include cimetidine, ranitidine, famotidine, omeprazole, and mixtures thereof. Other useful pharmaceutical actives include bismuth-containing agents such as, for example, bismuth subsalicylate, bismuth aluminate, bismuth citrate, bismuth subcitrate, bismuth nitrate, bismuth subcarbonate, bismuth subgalate, and mixtures thereof. A particularly preferred bismuth salt is bismuth subsalicylate.

In addition to antacid formulations, the personal care composition can be in the form of other types of medications, comprising other pharmaceutical actives. Such pharmaceutical actives can be added to the oil phase or water phase prior to the combination of these phases, or added after the phases are combined. Examples of pharmaceutical actives are those from the group consisting of acetaminophen, analgesics, appetite suppressants, antihistamines, central nervous system stimulants, deodorants, minerals, motion sickness agents, muscle relaxants, gastrointestinal agents, salts, sedatives, smoking cessation agents, vitamins, vertigo agents, acetyl-salicylic acid, ibuprofen, phenyl propanolamine, chloropheniramine, antibiotics, anticonvulsants, antidiabetics, antidotes, anti-infectives, anti-inflammatories, theophylline, antineoplastics, antiparkinsonian agents, antipsychotics, antirheumatics, antivirals, biological response modifiers, blood modifiers, cardioprotestive agents, cardiovascular agents, cerebral metabolic enhancers, cholesterol reducers, contraceptives, dopamine receptor agonists, erectile dysfunctional agents, fertility agents, galactorrhea inhibitors, gout agents, homeopathic agents, hormones, hyper- and hypocalcemia agents, hypnotics, immunodilators, immunosuppressives, migraine agents, narcotics, nucleosides, nutritional agents, ophthalmic agents, osteoporosis agents, oxytocics, parasympatholytics, parasympathomimetics, patent ductus arteriosus agents, porphyria agents, prostaglandins, psychotherapeutics, sympatholytics, triglyceride reducers, urinary tract agents, uterine relaxants, vasodilators, and the like, and combinations thereof.

In addition the pharmaceutical compositions may comprise excipients. The term "excipient(s)", as used herein, means, one or more compatible solid or liquid filler diluents or encapsulating substances which are suitable for oral administration to a human and encompasses all of the ingredients of the pharmaceutical compositions except the active pharmaceutical agent. The term "compatible", as used herein, means that the components of the compositions of the invention are capable of being commingled with the active pharmaceutical agent, and with each other, in a manner such that there is no interaction that would substantially reduce the pharmaceutical efficacy of the compositions under ordinary use situations. Excipients must, of course, be of sufficiently high purity and sufficiently low toxicity to render them suitable for administration to the human being.

Some examples of substances which can serve as excipients are malt; gelatin; talc; stearic acid; magnesium stearate; calcium sulfate; vegetable oils such as peanut oil, cottonseed oil, sesame oil, olive oil, corn oil and oil of theobroma; agar and alginic acid; as well as other non-toxic compatible substances used in pharmaceutical formulations. Wetting agents and lubricants such as sodium lauryl sulfate, as well as coloring agents, flavoring agents, tableting agents, stabilizers, antioxidants, and preservatives, can also be present.

The choice of excipients to be used in conjunction with the active pharmaceutical agent is basically determined by the dose form for the pharmaceutical compositions. Excipients suitable for the preparation of dosage forms for oral administration are well-known in the art. Their selection will depend on secondary considerations like taste, cost, shelf stability, and can be made without difficulty by a person skilled in the art.

In addition, the personal care compositions may in the form of soaps, shampoos, hair care products, cosmetics and the like. In these embodiments, active and inert ingredients of the soaps, shampoos, hair care products and cosmetics can be added to the oil phase or water phase prior to the combination of these phases, or added after the phases are combined. Also, the opacifying agent made by the modification of the process for making the water phase can be combined with finished bases to make a wide variety of consumer care products such as body washes, lotions, cosmetics, perfume, soap, shampoo, hair care products, and the like, and comestible goods such as beverages, sauces, gravies, food stuffs and the like.

EXAMPLES

Example 1

A personal care composition was made according to the invention by first making a water phase by combining 20 grams of sorbitol and 0.2 grams of saccharin with 148.16 grams of water in a mixer and mixing for about 10 minutes at ambient temperature, then adding a thickening agent comprising 0.24 grams of xanthan gum dispersed in 20 grams of glycerin with continued mixing for about 5 minutes at ambient temperature then adding 0.2 grams of titanium dioxide (U.S.P. available from Whittaker, Clark & Daniels) with continued mixing for about 10 minutes at ambient temperature. PURACAL® calcium lactate from PURAC was included in the water phase by adding 10 grams of the calcium lactate after the other ingredients are mixed with continued mixing for about 10 minutes at ambient temperature.

Separately, an oil phase was made by combining 10 grams of glycerin, 0.90 grams of CREMOPHOR® RH-60 (PEG-60 Hydrogeneated Castor Oil with an ethoxylation number of about 60) from BASF and 0.30 grams of flavoring in a mixer with mixing for about 10 minutes at ambient temperature. The water phase was then combined with the oil phase in the mixer and mixing continued for about 10 minutes at ambient temperature to obtain the personal care composition having a cloudy and milky appearance.

The personal care composition was then packaged in plastic 8 ounce bottles and observed for 36 hours. The composition maintained the cloudy and milky appearance for the 36 hour observation period and no settling or precipitation of the titanium dioxide was observed. The samples were observed for about a five month period and the samples maintained the cloudy and milky appearance and no settling or precipitation of the titanium dioxide occurred during the five month period.

Example 2

A personal care composition was made in accordance with the procedure of Example 1 except that 0.01 grams of FD&C Red No. 33 colorant was added to the water with the sorbitol and saccharin. The resulting personal care composition was cloudy and milky with a red tint. This personal care composition was then packaged in plastic 8 ounce bottles and observed for 36 hours. The composition maintained the cloudy and milky appearance for the 36 hour observation period and no settling or precipitation of the titanium dioxide occurred.

Example 3

A personal care composition was made according to the invention by first making a water phase by combining 20 grams of sorbitol and 0.3 grams of saccharin with 101.18 grams of water in a mixer and mixing for about 10 minutes at ambient temperature then adding a thickening agent comprising 0.24 grams of xanthan gum dispersed in 20 grams of glycerin with continued mixing for about 10 minutes at ambient temperature and then adding 0.2 grams of titanium dioxide (U.S.P. from Whittaker, Clark & Daniels) with continued mixing for about 10 minutes at ambient temperature.

Separately an oil phase was made by combining 45.4 grams of ethyl alcohol, 12.1 grams of water, 1.0 gram of CREMOPHOR® RH-60 from BASF and 0.58 grams of flavorings in a mixer with mixing for about 10 minutes at ambient temperature. The water phase was then combined with the oil phase in the mixer and mixing continued for about 10 minutes at ambient temperature to obtain the personal care composition having a cloudy and milky appearance. The composition was packaged in 8 ounce bottles. No settling or precipitation of the titanium dioxide was observed after 24 hours.

Example 4

A personal care composition was made according to the invention by first making a water phase by combining 42.24 grams of diglycerol and 0.30 grams of saccharin with 210 grams of water in a mixer and mixing for about 10 minutes at ambient temperature, then adding a thickening agent comprising 0.36 grams of xanthan gum dispersed in 15 grams of glycerin with continued mixing for about 5 minutes at ambient temperature and then adding 0.30 grams of titanium dioxide (U.S.P. available from Whittaker, Clark & Daniels) with continued mixing for about 10 minutes at ambient temperature. PURACAL® calcium lactate from PURAC was included in the water phase by adding 15 grams of the calcium lactate after the other ingredients are mixed with continued mixing for about 10 minutes at ambient temperature.

Separately, an oil phase was made by combining 15 grams of glycerin, 1.35 grams of CREMOPHOR® RH-40 (PEG-40 Hydrogenated Castor Oil with an ethoxylation number of about 40) from BASF and 0.45 grams of flavoring in a mixer with mixing for about 10 minutes at ambient temperature. The water phase was then combined with the oil phase in the mixer and mixing continued for about 10 minutes at ambient temperature to obtain the personal care composition having a cloudy and milky appearance.

The personal care composition was then packaged in plastic 8 ounce bottles, stored at 50° C. and observed for one week. The composition maintained the cloudy and milky appearance for the observation period and no settling or precipitation of the titanium dioxide was observed.

Example 5

In this example, an opacifying agent comprising 79% water, 20% glycerin, 0.5% xanthan gum and 0.50% titanium dioxide (U.S.P. available from Whittaker, Clark & Daniels) was prepared. The opacifying agent was made by first combining the water with half of the glycerin in a mixer and mixing for about 10 minutes at ambient temperature, then adding a thickening agent comprising the xanthan gum dispersed in the balance of the glycerin with continued mixing for about 5 minutes at ambient temperature and then adding the titanium dioxide with continued mixing for about 10 minutes at ambient temperature.

A milky and cloudy infant body wash was formed by combining 5% to 10% of the opacfying agent made by the process described in this Example with 90% to 95% of a finished base for infant body wash in plastic 8 ounce bottles and shaking the container until the contents of the bottles had a cloudy and milky appearance. The cloudy and milky infant body wash thus formed was observed for 36 hours. The composition maintained the cloudy and milky appearance for the 36 hour observation period and no settling or precipitation of the titanium dioxide was observed.

Example 6 (Comparative)

In this Example, the calcium lactate was added before the titanium dioxide. A first precursor composition was made by combining 10 grams of PURACAL® (calcium lactate) from PURAC, 10 grams of sorbitol and 0.10 grams of saccharin with 148.26 grams of water in a mixer and mixing for about 15 minutes at ambient temperature then adding a thickening agent comprising 0.24 grams of xanthan gum dispersed in 20 grams of glycerin with continued mixing for about 10 minutes at ambient temperature and then adding 0.2 grams of titanium dioxide (U.S.P. from Whittaker, Clark & Daniels) with continued mixing for about 10 minutes at ambient temperature. Separately, a second precursor composition was made by combining 10 grams of glycerin, 0.90 grams of CREMOPHOR® RH-60 and 0.30 grams of flavoring agent in a mixer with mixing for about 10 minutes at ambient temperature. The first and second precursor compositions were then combined and mixed for about 10 minutes at ambient temperature. The solution thus formed did not achieve a milky appearance. Also, when the titanium dioxide scattered in the first precursor composition and the titanium dioxide did not cloud or milk the system.

I claim:

1. A process for making a personal care composition having a cloudy and milky appearance comprising the steps of
    (a) combining about 30% to about 80% water, about 2% to about 25% of at least one water phase humectant and about 0.01% to about 0.50% of at least one sweetener and mixing, then adding about 0.01% to about 0.50% of at least one thickening agent dispersed in about 2.5% to about 10% of a carrier and continue mixing and then adding about 0.01% to about 1% titanium dioxide and continue mixing to obtain a water phase, and
    (b) separately combining about 0.1% to about 3% of at least one surfactant, about 0.01% to about 1% of at least one flavoring agent and about 1% to about 10% of at least one oil phase humectant and mixing to obtain an oil phase, and
    (c) combining and mixing the water phase and the oil phase to obtain the personal care composition
wherein the thickening agent comprises at least one hydrophilic colloid that forms a gel and the gel and titanium dioxide form a complex that allows the titanium dioxide to remain in suspension.

2. The process of claim 1 wherein about 0.5% to about 10% calcium lactate, calcium lactate salts or combinations thereof are added to the water phase with continued mixing in step (a) after the addition of the titanium dioxide.

3. The process of claim 1 wherein about 1.0% to about 30% alcohol is in the oil phase.

4. The process of claim 1 wherein fillers, additives, colorants, cooling agents, warming agents, numbing agents, additional flavorings, active compounds, excipients or combinations thereof are mixed with the components of the water phase or the oil phase before combination of the water phase and oil phase.

5. The process of claim 1 wherein step (c) comprises further combining fillers, additives, colorants, cooling agents, warming agents, numbing agents, additional flavorings, pharmaceutical actives, excipients or combinations thereof with the water phase and the oil phase.

6. The process of claim 1 wherein the sweetener is selected from the group consisting of saccharin, fructose, xylitol, saccharin salts, thaumatin, aspartame, D-tryptophan, dihydrochalcones, acesulfame, cyclamate salts, and combinations thereof.

7. The process of claim 1 wherein the hydrophilic colloid is selected from the group consisting of xanthan gum, polymeric polyesters, natural gums, carrageenan, hydroxymethyl cellulose, methyl cellulose, carboxymethylcellulose, arrowroot powder, starches and combinations thereof.

8. The process of claim 1 wherein the carrier is glycerin, polyethylene glycol or combinations thereof.

9. The process of claim 1 wherein the water phase humectant is selected from the group consisting of edible polyhydric alcohols, glycerin, glycerol, diglycerol, propylene glycol, propylene glycol glycerol, isomalt, xylitol, maltito, sorbitol, mannitol and combinations thereof.

10. The process of claim 1 wherein the oil phase humectant is selected from the group consisting of edible polyhydric alcohols, glycerin, glycerol, diglycerol, propylene glycol, propylene glycol glycerol, isomalt, xylitol, maltito, sorbitol, mannitol and combinations thereof.

11. The process of claim 1 wherein the surfactant is selected from the group consisting of ethoxylated hydrogenated castor oil, polyoxyethylene sorbitol monolaruin, polyoxyethylene sorbitol monopalmitate, polyoxyethylene sorbitol monostearin, polyoxyethylene sorbitol monolein, polysorbate 20–80, block polymers of polyoxyethylene and polyoxyproylene having a molecular weight between about 1,000 and about 15,000 and combinations thereof.

12. The process of claim 1 wherein the flavoring agent is selected from the group consisting of oil of peppermint, oil of wintergreen, oil of spearmint, clove bud oil, parsley oil, eucalyptus oil, menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanilla, thymol, linalool, cinnamaldehyde glycerol acetal and combinations thereof.

13. The process of claim 4 wherein the active compounds are pharmaceutical actives.

14. A personal care product made by the process comprising the steps of
(a) combining about 30% to about 80% water, about 2% to about 25% of at least one water phase humectant and about 0.01% to about 0.50% of at least one sweetener and mixing, then adding about 0.01% to about 0.50% of at least one thickening agent dispersed in about 2.5% to about 10% of a carrier and continue mixing and then adding about 0.01% to about 1% titanium dioxide and continue mixing to obtain a water phase, and
(b) separately combining about 0.1% to about 3% of at least one surfactant, about 0.01% to about 1% of at least one flavoring agent and about 1% to about 10% of at least one oil phase humectant and mixing to obtain an oil phase, and
(c) combining and mixing the water phase and the oil phase to obtain the personal care composition
wherein the thickening agent comprises at least one hydrophilic colloid that forms a gel and the gel and titanium dioxide form a complex that allows the titanium dioxide to remain in suspension.

15. A personal care product having a stable cloudy and milky appearance comprising about 30% to about 80% water, about 0.01% to about 0.50% of at least one sweetener, about 0.01% to about 0.50% of at least one thickening agent having at least one hydrophilic colloid dispersed in about 2.5% to about 10% of a carrier, about 0.01% to about 1% titanium dioxide, about 2% to about 25% of a water phase humectant, about 1% to about 10% of an oil phase humectant, about 0.1% to about 3% of at least one surfactant, about 0.01% to about 1% of at least one flavoring agent and, optionally, about 1.0% to about 10% calcium lactate, calcium lactate salts or combinations thereof, wherein the titanium dioxide is trapped in a gel matrix formed by the thickening agent that allows the titanium dioxide to remain in suspension.

16. The product of claim 15 further comprising from about 1.0% to about 30% alcohol.

17. The product of claim 15 further comprising fillers, additives, colorants, cooling agents, warming agents, numbing agents, additional flavorings, active compounds, excipients or combinations thereof.

18. The product of claim 15 wherein the sweetener is selected from the group consisting of saccharin, fructose, xylitol, saccharin salts, thaumatin, aspartame, D-tryptophan, dihydrochalcones, acesulfame, cyclamate salts, and combinations thereof.

19. The product of claim 15 wherein the hydrophilic colloid is selected from the group consisting of xanthan gum, polymeric polyesters, natural gums, carrageenan, hydroxymethyl cellulose, methyl cellulose, carboxymethylcellulose, arrowroot powder, starches and combinations thereof.

20. The product of claim 15 wherein the carrier is glycerin, polyethylene glycol or combinations thereof.

21. The product of claim 15 wherein the water phase humectant is selected from the group consisting of edible polyhydric alcohols, glycerin, glycerol, diglycerol, propylene glycol, propylene glycol glycerol, isomalt, xylitol, maltito, sorbitol, mannitol and combinations thereof.

22. The product of claim 15 wherein the oil phase humectant is selected from the group consisting of edible polyhydric alcohols, glycerin, glycerol, diglycerol, propylene glycol, isomalt, xylitol, maltito, sorbitol, mannitol and combinations thereof.

23. The product of claim 15 wherein the flavoring agent is selected from the group consisting of oil of peppermint, oil of wintergreen, oil of spearmint, clove bud oil, parsley oil, eucalyptus oil, menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanilla, thymol, linalool, cinnamaldehyde glycerol acetal and combinations thereof.

24. The product of claim 15 where in the surfactant is selected from the group consisting of ethoxylated hydrogenated castor oil, polyoxyethylene sorbitol monolaruin, polyoxyethylene sorbitol monopalmitate, polyoxyethylene sorbitol monostearin, polyoxyethylene sorbitol monolein, polysorbate 20–80, blockpolymer of polyoxyethylene and polyoxypropylene having a molecular weight between about 1,000 and 15,000 and combinations thereof.

25. The product of claim 17 wherein the active compounds are selected from the group consisting of chlorine dioxide, fluoride, alcohols, triclosan, domiphen bromide, cetyl pridinium chloride and combinations thereof.

26. The product of claim 17 wherein the active compounds are pharmaceutical actives.

27. The product of claim 21 wherein the pharmaceutical actives are selected from the group consisting of acetaminophen, analgesics, appetite suppressants, antihistamines, central nervous system stimulants, deodorants, minerals, motion sickness agents, muscle relaxants, gastrointestinal agents, salts, sedatives, smoking cessation agents, vitamins, vertigo agents, acetyl-salicylic acid, ibuprofen, phenyl propanolamine, chloropheniramine, antibiotics, anticonvulsants, antidiabetics, antidotes, anti-infectives, anti-inflammatories, theophylline, antineoplastics, antiparkinsonian agents, antipsychotics, antirheumatics, antivirals, biological response modifiers, blood modifiers, cardioprotestive agents, cardiovascular agents, cerebral metabolic enhancers, cholesterol reducers, contraceptives, dopamine receptor agonists, erectile dysfunctional agents, fertility agents, galactorrhea inhibitors, gout agents, homeopathic agents, hormones, hyper- and hypocalcemia agents, hypnotics, immunodilators, immunosuppressives, migraine agents, narcotics, nucleosides, nutritional agents, ophthalmic agents, osteoporosis agents, oxytocics, parasympatholytics, parasympathomimetics, patent ductus arteriosus agents, porphyria agents, prostaglandins, psychotherapeutics, sympatholytics, triglyceride reducers, urinary tract agents, uterine relaxants, vasodilators, and combinations thereof.

28. A process for making an opacifying agent for use with a finished base to provide a stable cloudy and milky appearance for a consumer care product or comestible good comprising the steps of combining about 30% to about 80% water and about 2% to about 25% of at least one water phase humectant and mixing, then adding about 0.01% to about 0.50% of at least one thickening agent having at least one hydrophilic colloid dispersed in about 2.5% to about 10% of a carrier and continue mixing, and then adding about 0.01% to about 1.0% titanium dioxide and continue mixing to obtain the opacifying agent wherein the hydrophilic colloid forms a gel and the gel and titanium dioxide is trapped in a gel matrix forming a complex that allows the titanium dioxide to remain suspension.

29. The process of claim 28 wherein the water phase humectant is selected from the group consisting of edible polyhydric alcohols, glycerin, glycerol, diglycerol, propylene glycol, propylene glycol glycerol, isomalt, xylitol, maltito, sorbitol, mannitol and combinations thereof.

30. The process of claim 28 wherein the hydrophilic colloid is selected from the group consisting of xanthan gum, polymeric polyesters, natural gums, carrageenan, hydroxymethyl cellulose, methyl cellulose, carboxymethylcellulose, arrowroot powder, starches and combinations thereof.

31. The process of claim 28 wherein the carrier is glycerin, polyethylene glycol or combinations thereof.

32. An opacifying agent for use with a finished base to provide a stable cloudy and milky appearance for a consumer care product or comestible good comprising about 30% to about 80% water, about 2% to about 25% of at least one water phase humectant, about 0.01% to about 0.50% of at least one thickening agent dispersed in about 2.5% to about 10% of a carrier and about 0.01% to about 1.0% titanium dioxide wherein the thickening agent comprises at least one hydrophilic colloid that forms a gel matrix and the titanium dioxide is trapped in the gel matrix forming a complex that allows the titanium dioxide to remain in suspension.

33. The opacifying agent of claim 32 further comprising from about 0.5% to about 10% calcium lactate, calcium lactate salts or combinations thereof.

34. The opacifying agent of claim 32 wherein the water phase humectant is selected from the group consisting of edible polyhydric alcohols, glycerin, glycerol, diglycerol, propylene glycol, propylene glycol glycerol, isomalt, xylitol, maltito, sorbitol, mannitol and combinations thereof.

35. The opacifying agent of claim 32 wherein the hydrophilic colloid is selected from the group consisting of xanthan gum, polymeric polyesters, natural gums, carrageenan, hydroxymethyl cellulose, methyl cellulose, carboxymethylcellulose, arrowroot powder, starches and combinations thereof.

36. The opacifying agent of claim 32 wherein the carrier is glycerin, polyethylene glycol and combinations thereof.

37. A consumer care product or comestible good comprising the opacifying agent of claim 32.

38. A process for making a personal care composition having a cloudy and milky appearance comprising the steps of
   (a) combining about 30% to about 80% water, about 2% to about 25% of at least one water phase humectant and about 0.01% to about 0.50% of at least one sweetener and mixing, then adding about 0.10% to about 0.50% of at least one thickening agent dispersed in about 2.5% to about 10% glycerin and continue mixing and then adding about 0.01% to about 1% titanium dioxide and continue mixing and then adding about 0.5% to about 10% calcium lactate, calcium lactate salts or combinations thereof with continued mixing to obtain a water phase, and
   (b) combining in a second means for mixing about 0.1% to about 3% of at least one surfactant, about 0.01% to about 1% of at least one flavoring agent and about 1% to about 10% of at least one oil phase humectant and mixing to obtain an oil phase, and
   (c) combining and mixing the water phase and the oil phase in either the first or second rreans for mixing or a separate means for mixing, and mixing the water phase and oil phase to obtain the personal care composition wherein the thickening agent comprises at least one hydrophilic colloid that forms a gel and the gel and the titanium dioxide form a complex that allows the titanium dioxide to remain in suspension.

39. The process of claim 38 wherein the oil phase comprises about 1.0% to about 30% alcohol.

40. A process for making an opacifying agent for use with a finished base to provide a stable cloudy and milky appearance for a consumer care product or comestible good comprising the steps of combining about 30% to about 80% water and about 2% to about 25% of at least one water phase humectant and mixing, then adding about 0.01% to about 0.50% of at least one thickening agent having at least one hydrophilic colloid dispersed in about 2.5% to about 10% of a carrier and continue mixing, then adding about 0.01% to about 1.0% titanium dioxide and continue mixing and then adding about 0.5% to about 10% calcium lactate, calcium lactate salts or combinations thereof with continued mixing to obtain the opacifying agent wherein the hydrophilic colloid forms a gel and the gel and the titanium dioxide form a complex that allows the titanium dioxide to remain in suspension.

* * * * *